United States Patent [19]

Paciorek et al.

[11] Patent Number: 4,946,809
[45] Date of Patent: Aug. 7, 1990

[54] PRECURSOR FOR A1NBN CERAMIC AND METHOD OF USE

[75] Inventors: Kazimiera J. L. Paciorek, Corona del Mar; James H. Nakahara, Irvine, both of Calif.

[73] Assignee: Ultraystems Defense and Space, Inc., Irvine, Calif.

[21] Appl. No.: 358,063

[22] Filed: May 26, 1989

[51] Int. Cl.$^5$ ................................................ C07F 5/06
[52] U.S. Cl. ........................................ 556/173; 501/96;
501/98; 501/100; 501/153; 427/190; 427/199; 428/128
[58] Field of Search ............... 501/96, 98, 100, 153; 427/190, 199, 215, 226; 428/128, 604; 556/173

[56] References Cited

U.S. PATENT DOCUMENTS

| | | | |
|---|---|---|---|
| 4,581,468 | 4/1986 | Paciorek et al. | 556/403 |
| 4,642,271 | 2/1987 | Rice | 428/698 |
| 4,666,873 | 5/1987 | Morris, Jr. et al. | 501/96 |
| 4,707,556 | 11/1987 | Paciorek et al. | 556/403 |
| 4,764,489 | 8/1988 | Bolt | 501/96 |

*Primary Examiner*—William R. Dixon, Jr.
*Assistant Examiner*—Chris Gallo

[57] ABSTRACT

A soluble, processible ceramic precursor, comprising A1N and BN in fixed proportion, which on pyrolysis is transformed into pure carbon free A1NBN ceramic, of the formula:

$$R_3N \cdot X_2A1n(SiR'_3)B(NH_2)NHSiR'_3$$

wherein R and R' are independently lower alkyl groups or isomers thereof having from one to about five carbon atoms.

Also disclosed are methods for making the precursor, and methods for thermally decomposing the precursor to form coatings, thin films, and shaped articles of substantially pure A1NBN ceramic.

12 Claims, No Drawings

PRECURSOR FOR AlNBN CERAMIC AND METHOD OF USE

RIGHTS OF THE GOVERNMENT

This invention was made with government support under Contract No. F49620-85-C-0042 awarded by the Department of the Air Force. The United States government has certain rights in this invention.

FIELD OF THE INVENTION

This invention relates to the synthesis of processible precursors for mixed ceramic compounds, particularly for compounds comprising AlN and BN in a defined ratio, and useful applications thereof.

BACKGROUND OF THE INVENTION

Ceramic compounds such as the nitrides of boron, aluminum and silicon (BN, AlN, and $Si_3N_4$) and the carbides of boron and silicon ($B_4C$ and SiC) have high thermal stability and are impervious to chemical attack, properties which make them commercially important. However, their related properties of insolubility and infusibility make it difficult to process these materials into useful end products.

Ceramic compounds provide protective coatings for less stable structural materials, thereby expanding their useful applications. While the formation of composite materials utilizing alumina fibers is well known, alumina can form an eutectic at elevated temperatures when in an oxide matrix. Carbon fibers possess many desirable properties, including high temperature stability and mechanical strength. Unfortunately, unprotected carbon fibers are unstable in oxidizing atmospheres. However, articles made of carbon or alumina and coated with ceramic, such as BN or AlN, remain intact, thus retaining their mechanical strength on exposure to conditions at which the uncoated material would melt or oxidize. Present methods of forming a ceramic coating on these materials usually require chemical vapor deposition which is costly and difficult to control.

A readily processible precursor, which upon pyrolysis could be transformed into a ceramic, would offer specific potential for coating fibers, irregular shapes, producing thin films, and also as a binder for ceramic powders, eliminating the use of additives or sintering aids.

Soluble processible ceramic precursors of particular commercial interest are those which can be pyrolyzed to yield materials such as SiC, $Si_3N_4$, as well as materials such as BN, AlN, $B_4C$ and AlNBN. It is important, however, in order to produce a ceramic with desirable properties, that these precursors can be pyrolyzed to a pure ceramic, free of carbon and other impurities that affect its physical properties. The inventors have produced soluble and fusible borazine polymers capable of transformation into carbon-free boron nitride by the synthesis of B-triamino-N-tris (trialkylsilyl) borazines and silylamino-substituted borazines, and subsequent thermal condensation of these compounds into preceramic polymers. These soluble processible preceramic polymers, which produce pure BN ceramic on pyrolysis, are the subject of U.S. Pat. Nos. 4,581,468 and 4,707,556 to Paciorek et al.

Certain ceramic compounds frequently provide superior durability and heat resistance when combined with another in a defined stoichiometry. Soluble processible preceramic polymers comprising defined molar ratios of SiC and $Si_3N_4$ and which produce mixed SiC and $Si_3N_4$ on pyrolysis are the subject of U.S. Pat. No. 4,719,273 to Seyferth et al.

A readily processible precursor which upon pyrolysis can be transformed into a novel pure mixed ceramic offers a potential for applications which cannot be met by a single material such as either AlN or BN.

It is therefore a principal object of the invention to provide a suitable precursor of a mixed boron nitride and aluminum nitride ceramic which is soluble in organic solvents, which thus can be used to coat fibers, densify porous materials, or form ceramic coatings including thin films, on surfaces of materials.

It is also an object of the invention to provide processes for transforming the mixed boron nitride and aluminum nitride ceramic precursor into coatings and shaped articles of pure mixed boron and aluminum ceramic.

It is also an object of the present invention to provide a processible precursor for a novel mixed boron nitride and aluminum nitride ceramic having new and useful properties, whose subsequent pyrolysis provides a high yield of pure ceramic.

SUMMARY OF THE INVENTION

The present invention resides in the synthesis of a ceramic precursor of the formula

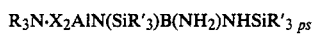

wherein R and R' are independently $C_1$ to $C_5$ alkyl or isomeric forms thereof, and X is Br or Cl. In preferred embodiments, R is ethyl and R' is methyl.

There is provided also a method of synthesizing this ceramic precursor by reacting a metal disilazane having the formula $LiN(SiR'_3)_2$ with a halogenated silylamino aluminum having the formula $(X_2AlNHSiR'_3)_2$ to form a reaction product having the formula $[(R'_3Si)_2NAlNSiR'_3]_2$, wherein R' is $C_1$ to $C_5$ alkyl and X is Cl or Br; contacting the reaction product with ammonia to form an ammonolysis product having the formula

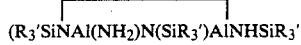

wherein R' is as defined above; and reacting said ammonolysis product with a (disilylamino)aminosilylchloroborane of the formula $(R'_3Si)_2NB(X)NHSiR'_3$ and an amine of the formula $NR_3$, wherein $R_3$ is $C_1$ to $C_5$ alkyl or isomeric forms thereof, to form the ceramic precursor of claim 1.

In one embodiment, the first step of the synthesis is carried out under an inert atmosphere comprising a gas or a mixture of gases selected from nitrogen, helium and argon at about ambient pressure. In a preferred embodiment, the halogenated silylamino aluminum (compound I) and the lithium disilazane salt are reacted in benzene for a period of from between about 2 to about 24 hours at a temperature from about 0° to about 50° C. In another embodiment, the second step of the synthesis, comprising the reaction of the ammonolysis product with a (disilylamino)aminosilylchloroborane and an amine is carried out in an atmosphere of ammonia. In a preferred embodiment, the reactions are carried out at ambient pressure.

In accordance with another object of the invention there is provided a process of preparing AlNBN ceramic from the ceramic precursor by heating the precursor to a sufficient degree to effect the conversion. In a preferred embodiment, the process comprises gradually heating the precursor in a system having an atmosphere of either inert or reactive gas at a rate to bring the temperature of the system to about 1000° C. in a period of 1 to 8 hours. In particularly preferred embodiments, the inert atmosphere comprises a gas or a mixture of gases selected from nitrogen, helium and argon and is at a pressure between about 400 mm Hg and 760 mm Hg. In other embodiments, the inert gas is replaced by ammonia after the precursor has been heated to between 300° and 400° C. The ammonia gas is maintained in the same pressure range listed above.

According to yet another aspect of the invention there is provided substantially pure AlNBN ceramic. In a preferred embodiment the AlNBN ceramic is prepared by the method of the invention.

We have found that it is possible to make shaped and coated articles from the AlNBN precursor of the invention.

Accordingly, there is provided a process for coating an object with AlNBN ceramic, comprising applying to the object the AlNBN precursor in solution to coat the object with the precursor; and heating the precursor coated object to convert the ceramic precursor to AlNBN ceramic. The final stage of the coating process, in which the preceramic material is thermally converted into AlNBN ceramic by heating to a temperature of about 1000° C., is carried out either entirely under an inert gas or under inert gas for the initial stage of heating, in which case the system is cooled and the inert gas replaced by ammonia before heating to higher temperatures.

In accordance with yet another object of the invention, there are provided shaped articles of AlNBN and alumina fibers or carbon fibers coated with AlNBN. In a preferred embodiment, the shaped articles are formed from the ceramic precursor of AlNBN. In another preferred embodiment, the alumina fibers or carbon fibers are coated with substantially pure AlNBN according to the process of the invention.

DETAILED DESCRIPTION OF THE PREFERRED EMBODIMENT

We have discovered that the reaction of a dichlorosilylamino aluminum with a lithium salt of a disilazane followed by ammonolysis and condensation with a silylamino-substituted haloborane results in novel ceramic precursors that have many useful applications. The novelty of the invention resides principally in the combination of AlN and BN in fixed proportion in a preceramic compound. The pyrolysis of the preceramic compound leaves only substantially pure carbon-free AlNBN ceramic. Further, the solubility of these preceramic compounds in organic solvents permits improved processes that provide specialized features and properties. The present invention resides in the synthesis of the ceramic precursor of the formula $R_3N \cdot X_2AlN(SiR'_3)B(NH_2)NHSiR'_3$ wherein R and R' are independently $C_1$ to $C_5$ alkyl groups or isomers thereof, and X is a halogen such as chlorine or bromine. Preferably R and R' are independently alkyl groups such as methyl, ethyl, or propyl, and X is chlorine.

The following reaction represents the synthesis process:

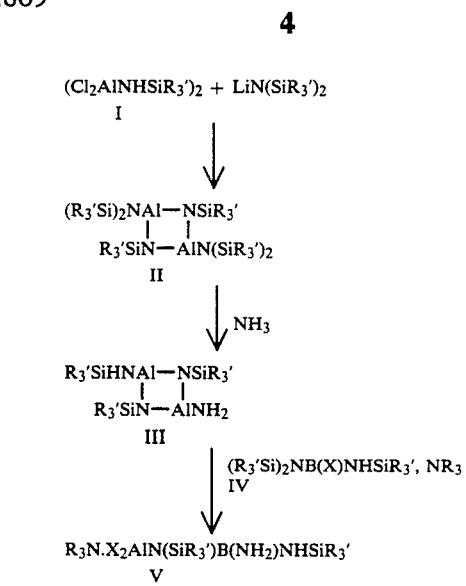

The procedure followed in the synthesis of the ceramic precursor consists of the preparation of the four-membered ring compound II by reaction of the dichloroaluminum compound I described by N. Wiberg and K. H. Schmidt, Z. Anorg. allg. Chem., 345 93–104 (1966) with lithium salt of hexamethyldisilazane, described in Inorganic Syntheses, 8: 20–22 (1966). This reaction is preferably conducted at temperatures ranging from about 0° C. to about 50° C. for a period from about 2 to about 24 hours, although longer or shorter time periods are acceptable.

The subsequent ammonolysis to form compound III is preferably performed at a temperature ranging from about −78° C. to about 25° C. over a time period of about 4 to about 24 hours, although longer or shorter time periods are acceptable. To obtain the ceramic precursor, compound V, the compound III is reacted with compound IV, preferably bis(trimethylsilyl)amino-trimethylsilylaminochloroborane, described by R. L. Wells and A. L. Collins, Inorg. Chem., 5, 1327–1328 (1966) preferably at a temperature ranging from about 20° C. to about 75° C. for a time period from about 4 to about 75 hours in the presence of an amine, preferably a tertiary amine $NR_3$ such as triethylamine. Each of the steps delineated above are carried out either in vacuo, or under an inert gas such as nitrogen, helium or argon, or a mixture of these gases, at pressures which can be as high as ambient or greater.

To obtain the final ceramic desired from the precursor, either in bulk form or as a coating on articles, the material or composition is preferably heated gradually over a time period of about 4 to about 24 hours between a temperature from about 25° C. to about 1000° C., yet any applicable method of ceramic pyrolysis is contemplated. The pyrolysis is preferably carried out in an inert gas such as nitrogen, helium or argon, or the final stages of the pyrolysis may be carried out under an atmosphere of ammonia. Either a vacuum or an atmosphere of an inert gas is preferred under flow conditions; however, under static conditions, an atmosphere of ammonia is preferred in order to assure complete carbon removal.

Preferably, the dihalosilylamino aluminum is of the formula $(X_2AlNHSiR'_3)_{2'}$, wherein R' is a $C_1$ to $C_5$ alkyl group or an isomer thereof, and X is a halogen, preferably chlorine or bromine. Preferably, R' is a methyl group.

The lithium salt of the organic disilazane has the formula $LiN(SiR'_3)_2$, wherein R' is as defined above. Again, preferably, R' is a methyl group.

Although smaller $R_1$ groups, such as methyl are preferred in the preceramic material in order to avoid carbon retention in the ceramic, R groups larger than methyl could produce a preceramic material which is more soluble.

Compound II is then reacted with ammonia in such a solvent to effect the ammonolysis reaction. The ammonolysis reaction of the four membered ring compound II is carried out in any organic solvent in which the reactants are soluble. Solvents which may be used include: dialkyl ethers, particularly diethyl ether; aliphatic hydrocarbons such as hexanes and heptanes; aromatic hydrocarbons such as benzene, toluene, and xylenes. Other useful solvents are well known to the person of ordinary skill in the art, based upon this disclosure.

In a preferred embodiment of the present invention, the product III is treated with quantities of the compound $(R'_3Si)_2NB(X)NHSiR'_3$, IV wherein R' is a $C_1$ to $C_5$ alkyl group or isomer thereof, and X is a halogen, preferably chlorine or bromine. Preferably, R' is $CH_3$. The reaction is carried out in the presence of an amine, preferably a tertiary amine, $NR_3$, such as triethylamine, neat, or in an organic solvent. This reaction preferably results in the preceramic polymer V.

The ammonolysis product is reacted with the base and the haloborane, either neat or in any organic solvent in which the product is soluble without reaction. Such organic solvents include ethers, such as dialkyl ethers, preferably diethyl ether, aliphatic hydrocarbons such as hexane and heptane, arenes, such as benzene and toluene, and combinations thereof.

The methods described herein, particularly in Example I, generally result in the formation of precursors of mixed AlNBN ceramic in yield of approximately 60 to 90%. These precursors are pyrolyzed in nitrogen, an inert atmosphere, or a reactive atmosphere such as ammonia for a sufficient time and at a sufficient temperature to form a ceramic product. If an ammonia atmosphere is used in the pyrolysis, the ammonia gas is not introduced until after an initial period of heating to between about 300°-400° C. under an inert atmosphere, so as to first remove the halide-containing byproducts. On pyrolysis, the silicon, carbon, and halogen introduced by means of the alkyl-containing silyl groups combine, so that the ceramic product is virtually free of these contaminants, as indicated in Example II.

The soluble ceramic precursors of the present invention, comprising AlN and BN ceramic as a compound or mixture in approximately equal molar ratios, may be used to provide novel AlNBN ceramic coatings that are substantially free of defects. The soluble precursor, because of its ability to penetrate small channels, can also provide the densification of foams and porous composites. For example, the AlNBN precursor in solution can be used to infiltrate porous ceramic bodies formed under pressure from ceramic powders. Its fluid property also facilitates the production of very thin AlNBN ceramic films, an embodiment not possible by means of powder ceramic processes.

Accordingly, the present invention also includes AlNBN fabrications, comprising coatings and shaped articles which can be prepared from the synthesized soluble AlNBN precursor. The procedures for preparing these fabrications are similar to those presented in a co-pending application U.S. application Ser. No. 120,335, which discloses the preparation of BN ceramic fabrications from soluble BN precursor polymers.

Applications for a soluble AlNBN precursor which can be thermally converted into an AlNBN ceramic, fabricated according to these procedures, include, among others, the formation of the ceramic into complex shapes, either alone or in combination with other ceramic materials; as a matrix for carbon or ceramic fibers or as a binder for ceramic powders; the production of oxidation resistant coatings on otherwise oxidizable materials such as carbon composites or other materials containing carbon; impervious ceramic coatings of eutectic forming or reactive materials such as alumina; as an infiltrate for porous bodies of other ceramic materials; and the formation of thin films which can be applied, for example, in the manufacture of electronics components.

One of the more useful applications of AlNBN ceramics is to provide a protective coating on material so as to prevent chemical or physical change. An AlNBN ceramic coating can provide a barrier to prevent an undesired interaction (such as a chemical reaction or dissolution) between two otherwise incompatible materials; for example, a fiber and the matrix in which it is embedded. It may also act as an electrical insulator. The soluble preceramic AlNBN precursor herein described is particularly well suited to such coating applications.

AlNBN coatings may be applied to articles by dipping the article into a solution of AlNBN precursor, and then curing the precursor by thermal transformation to form a coat of substantially pure AlNBN ceramic, as described in Example II. Other methods of application, such as painting, spraying and the like are also contemplated.

A specific application is in the coating of carbon or alumina fibers. The soluble processible AlNBN ceramic precursor is particularly effective in providing ceramic coatings that are able to preserve the structure of alumina fibers within an oxide matrix. Unprotected alumina fibers dissolve at temperature below the melting point of alumina in the presence of an oxide such as silica because of the formation of an eutectic mixture of the oxides. An AlNBN ceramic coating on alumina fibers, however, creates a protective barrier that permits their use in oxide-type composites. Alumina fibers, when coated with AlNBN, can be used in glass matrices which would otherwise dissolve them. Example III provides a procedure for coating such fibers. Glass or ceramic matrices incorporating such fibers, which can be made using well known techniques, are also contemplated. Carbon fibers, when coated with ceramic, can perform in oxidizing atmospheres in which carbon alone cannot survive. Carbon fibers may be coated in a procedure similar to that for alumina, as described in Example IV.

Because the coefficient of thermal expansion of AlNBN is low relative to many other materials, and because of the high thermal stability of the material, thin films of AlNBN may find particular utility not only in electronics applications, but such thin films and shaped articles comprising AlNBN ceramic may be useful as coatings or elements of components of internal combustion engines, and in other applications where these physical characteristics are important.

EXAMPLE I

Preparation of
$(C_2H_5)_3N \cdot Cl_2AlN(Si(CH_3)_3)B(NH_2)NHSi(CH_3)_3$ 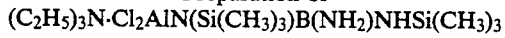

In an inert atmosphere at room temperature, to a stirred solution of lithium salt of hexamethyldisilazane (36.01 g, 215.2 mmol) in benzene (100 ml) was added slowly, over 30 min., [$(CH_3)_3SiNHAlCl_2]_2$ (20.01 g, 53.76 mmol) in benzene (100 ml). After stirring at room temperature for 24 hours, the precipitate [mainly lithium chloride (11.2 g)] was filtered off. Removal of solvent in vacuo yielded 27.6 g of a pale yellow solid. Washing with Freon-113 gave 18.56 g (62.9% yield) of [$(CH_3)_3SiNAlN(Si(CH_3)_3)_2]_2$, mp 186°–197° C. Anal. Calcd. for $C_9H_{27}N_2Si_3Al$: N, 10.20, MW:549.74. Found: N, 10.6 MW:548 (mass spectrometry).

Subsequently, in an inert atmosphere enclosure into a 200 ml round bottom flask equipped with a stirring bar was introduced (10.10 g, 18.39 mmol) of [$(CH_3)_3SiNAlN(Si(CH_3)_3)_2]_2$, the above compound II, followed by hexane (48.68 g). The apparatus was then attached to a vacuum system, cooled to −78° C. and the nitrogen removed. At that stage the contents were warmed to 0° C. and allowed to react with ammonia (0.67 g, 39.64 mmol). For the first hour the reaction was conducted at 0° C. then it was allowed to warm up at room temperature for a total reaction time of 16 hours. The excess ammonia was removed in vacuo at −78° C.; the solvent at room temperature. The liquid residue was heated in vacuo at 85° C. for 16 hours; 6.56 g of solid remained. This material was treated with Freon-113 (45 ml) in an inert atmosphere enclosure; an insoluble solid (0.87 g) was removed by filtration. The filtrate on evaporation gave 5.76 g (93.5%) of the product,

$(CH_3)_3SiNAl(NH_2)N(Si(CH_3)_3)AlNSi(CH_3)_3$, compound III, mp 195°–218° C. (dec). Anal. Calcd. for $C_9H_{30}N_4Al_2Si_3$: C, 32.50; H, 9.09; N, 16.85. Found: C, 31.27; H, 9.13; N, 16.90.

A mixture of

$(CH_3)_3SiNAl(NH_2)N(Si(CH_3)_3)AlNSi(CH_3)_3$ (2.09 g, 6.29 mmol), triethylamine (1.31 g, 12.94 mmol), and $((CH_3)_3Si)_2NBClNHSi(CH_3)_3$ (7.33 g, 24.87 mmol) was heated in an evacuated, sealed ampoule at 63°–67° C. for 24 hours. During that period, deposition of a solid was observed. After removal in vacuo of the volatiles the residue was treated with pentane (in an inert atmosphere enclosure), yielding 3.85 g (76.4% yield) of $(C_2H_5)_3N \cdot Cl_2AlN(Si(CH_3)_3)B(NH_2)NHSi(CH_3)_3$, compound V. Anal. Calcd. for $C_{12}H_{36}N_4Cl_2BAlSi_2$: C, 35.91; H, 9.04; N(NH_3), 10.47; Cl, 17.70; B, 2.74. Found: C, 35.82; H, 9.45; N(NH_3), 10.7; Cl, 17.8; B, 2.65.

EXAMPLE II

AlNBN Production from a Ceramic Precursor

The ceramic precursor, described in Example 1, 23.07 mg was heated in nitrogen atmosphere from room temperature to 1000° C. at the rate of 10° C./min using DuPont 990 system and 951 thermogravimetric analysis module. The grey-white residue amounted to 16.2% of the material employed. Calcd. for $C_{12}H_{36}N_4Cl_2BAlSi_2$ →AlNBN residue 16.16%. This material did not melt or lose any weight when heated in air at 1000° C.

EXAMPLE III

AlNBN Production from a Ceramic Precursor under an Ammonia Atmosphere

The ceramic precursor, described in Example I, 520 mg, was heated in a quartz tube under vacuum from room temperature to 330° C. in 1 hour, and maintained at that temperature for 4 hours. After removal of volatiles, 500 mm of ammonia was added to the tube containing the precursor which was then heated from room temperature to 1000° C. over a period of 4 hours. The residue was subsequently heated in a nitrogen atmosphere from room temperature to 1000° C. in 1.5 hours; a white solid resulted. The solid was shown by X-ray powder diffraction to consist of AlN and BN.

d-values for AlN (hex): 2.70, 2.49, 2.37, 1.83, 1.56, 1.41, 1.32; Found: 2.70, 2.3–2.5, 1.83, 1.52, 1.40, 1.32; d-values for BN (hex): 3.33; Found: 3.3.

EXAMPLE IV

AlNBN Coated Carbon Fiber

A 200-filament section of a yarn of continuous polycrystalline carbon fibers is heated gradually in a quartz tube from 25° to 620° C. in an air atmosphere over 3.5 hours to remove any surface coating. Subsequently, the system is evacuated and the temperature raised to 985° C. over 3.5 hours. After the system is cooled to room temperature, it is brought to atmospheric pressure by introducing nitrogen. The heat-treated fibers are then dipped into a benzene solution containing 2 to 10% by weight of the aluminum nitride-boron nitride ceramic precursor under conditions of a nitrogen or inert atmosphere. The transformation of the preceramic coating to pure aluminum nitride-boron nitride is accomplished by gradual heating first from about 25° C. to about 350° C. under an inert atmosphere, followed by cooling to room temperature, and next heating to 977° C. over an 8-hour period in an ammonia atmosphere, 500 mm Hg. The system is cooled under vacuum to room temperature and brought to atmospheric pressure with nitrogen. In this manner, carbon fibers coated by aluminum nitride-boron nitride are produced.

What is claimed is:

1. A ceramic precursor of the formula $R_3N \cdot X_2AlN(SiR'_3)B(NH_2)NHSiR'_3$ 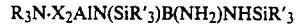

wherein R and R' are independently $C_1$ to $C_5$ alkyl or isomeric forms thereof, and X is Br or Cl.

2. The ceramic precursor of claim 1 wherein R is ethyl and R' is methyl.

3. The process of preparing the ceramic precursor of claim 1, comprising the steps of:
   (a) reacting a disilazane having the formula $LiN(SiR'_3)_2$ with a halogenated silylamino aluminum having the formula $(X_2AlNHSiR'_3)_2$ to form a reaction product having the formula $[(R'_3Si)_2NAlNSiR'_3]_2$, wherein R' is $C_1$ to $C_5$ alkyl and X is Cl or Br;

(b) contacting said reaction product with ammonia to form an ammonolysis product having the formula

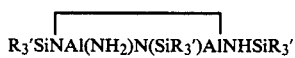

wherein R' is as defined above; and
(c) reacting said ammonolysis product with a (disilylamino)aminosilyl-chloroborane of the formula $(R'_3Si)_2NB(X)NHSiR'_3$ and an amine of the formula $NR_3$, wherein R is $C_1$ to $C_5$ alkyl, to form the ceramic precursor of claim 1.

4. The process of claim 3 wherein step (a) is carried out under an inert atmosphere comprising a gas or a mixture of gases selected from nitrogen, helium and argon.

5. The process of claim 3 wherein step (b) is carried out in an atmosphere of ammonia.

6. The process of claim 4 or 5 wherein said gas or said mixture of gases is at ambient pressure.

7. The process of claim 3 wherein in step (a), said halogenated silylamino aluminum and a lithium disilazane salt are reacted in benzene for a period of from between about 2 to about 24 hours at a temperature from about 0° to about 50° C.

8. A process for preparing a AlNBN ceramic material from the precursor of claim 1, comprising the step of heating said precursor to a sufficient degree to effect the conversion.

9. The process of claim 8, wherein said heating step comprises gradually heating said precursor in a system having an atmosphere of an inert gas at a rate to bring the temperature of said system to about 1000° C. in a period of from about 1 to 8 hours.

10. The process of claim 9 wherein said atmosphere is at a pressure between about 400 mm Hg and 760 mm Hg.

11. The process of claim 9 wherein said inert atmosphere comprises a gas or a mixture of gases selected from nitrogen, helium and argon.

12. The process of claim 11 wherein said inert gas is replaced by ammonia when the temperature of the system exceeds about 300° C.

* * * * *